United States Patent
Seo et al.

[11] Patent Number: 5,905,177
[45] Date of Patent: May 18, 1999

[54] METHOD FOR PRODUCING 1,2-DICHLOROETHANE

[75] Inventors: Ikuya Seo; Terumasa Yoshida, both of Shinnanyo, Japan

[73] Assignee: Toshoh Corporation, Japan

[21] Appl. No.: 08/616,453

[22] Filed: Mar. 15, 1996

[30] Foreign Application Priority Data

Apr. 20, 1995 [JP] Japan .................................. 6-94974

[51] Int. Cl.$^6$ ............................ C07C 17/15; C07C 17/02
[52] U.S. Cl. ........................ 570/243; 570/245; 570/246
[58] Field of Search ................................ 570/243, 246, 570/245

[56] References Cited

U.S. PATENT DOCUMENTS 4,265,837  5/1981  Legutke et al. .................... 570/243
4,788,359  11/1988  Schuchandt et al. .................... 570/243

FOREIGN PATENT DOCUMENTS 0 146 925   7/1985   European Pat. Off. .
2 314 907   6/1976   France .
1189815     4/1970   United Kingdom .

*Primary Examiner*—Shean C. Wu
*Attorney, Agent, or Firm*—Nixon & Vanderhye

[57] ABSTRACT

In a method for producing 1,2-dichloroethane by an oxychlorination reaction of ethylene, hydrogen chloride and oxygen, a continuous method for producing 1,2-dichloroethane, which comprises cooling a gas discharged from an oxychlorination reactor to condense and separate 1,2-dichloroethane and water therefrom, further removing hydrogen chloride and carbon dioxide therefrom, then mixing oxygen and nitrogen thereto so that the oxygen concentration becomes from 20 to 30 vol % and the ethylene concentration becomes from 1 to 3 vol % and supplying the gas mixture thus adjusted to an oxychlorination reactor.

8 Claims, 4 Drawing Sheets

METHOD FOR PRODUCING 1,2-DICHLOROETHANE

BACKGROUND OF THE INVENTION

The present invention relates to a method for continuously producing 1,2-dichloroethane (hereinafter referred to as EDC) efficiently by using hydrogen chloride produced in a large amount as a by-product at the time of producing a vinyl chloride monomer by thermally decomposing EDC, by a so-called oxychlorination reaction (hereinafter referred to simply as the oxy reaction) for producing EDC by reacting such hydrogen chloride with ethylene and oxygen, whereby the ethylene yield and the hydrogen chloride yield are substantially improved, while avoiding a dangerous state such as burning or explosion of ethylene with oxygen and substantially reducing the amount of a gas discharged out of the system (hereinafter referred to as the waste gas) at the time of carrying out the reaction.

To carry out the oxy reaction of ethylene, hydrogen chloride and oxygen, a so-called air method wherein air is used for oxygen as one of the raw materials and an oxygen method wherein oxygen is preliminarily separated from air and the separated oxygen is used, are widely employed for practical use as typical industrial processes. In such industrial processes for the oxy reaction, it is common to provide a waste gas treating installation such as a waste gas incinerator and an installation for recovering chlorinated hydrocarbons such as EDC, and hydrocarbons such as ethylene remaining unreacted, so that such chlorinated hydrocarbons and hydrocarbons will not be discharged directly into the atmosphere.

In the case of the air method, an inert gas such as nitrogen will be introduced in a large amount to the oxy reactor together with the supplied oxygen source, whereby the amount of the waste gas discharged out of the system will correspondingly be large, and large scale installations are required for waste gas treatment and recovery of EDC, etc.

On the other hand, the oxygen method has a merit in that the amount of the waste gas can substantially be reduced by preliminarily removing the inert component such as nitrogen, whereby the waste gas treating installation can substantially be scaled down. For this reason, an attention has been drawn to this oxygen method in recent years.

Further, depending upon the differences in the structure of the reactors themselves, the oxy reaction processes are practically conducted in a so-called fluidized bed system, whereby the oxy reaction is carried out while fine catalyst particles are fluidized in a reactor, or a fixed bed system wherein a particulate catalyst is packed in metal tubes and the reaction is carried out while circulating a heat medium around the tubes to remove the heat generated by the reaction.

As an oxygen method employing a fluidized bed reactor, Japanese Examined Patent Publication No. 1299/1988 discloses a method for producing EDC continuously, which comprises introducing pure oxygen, ethylene and hydrogen chloride to conduct the oxy reaction and then cooling the reaction gas discharged from the reactor to condense and separate EDC and water contained therein, and recycling the majority of non-condensed gas (hereinafter referred to as the recycling gas) to the reactor to e.g. fluidize the catalyst.

Further, as an oxygen method employing a fixed bed reactor, U.S. Pat. No. 3,892,816 discloses a method wherein the ethylene concentration in the recycling gas is adjusted to be at least 50%, so that the ethylene concentration in the reaction zone in the system is maintained constantly at least 70%, and oxygen is introduced dividedly to a plurality of reactors so that the concentration will be lower than the level for burning or explosion, and Japanese Unexamined Patent Publication No. 134295/1994 discloses a production method wherein the ethylene concentration in the recycling gas is maintained to be from 1 to 10 vol %, and the oxygen concentration is maintained to be from 0.5 to 7 vol %.

However, in the oxygen method disclosed in Japanese Examined Patent Publication No. 1299/1988, a fluidized bed reactor is employed, and therefore, the catalyst is likely to be finely pulverized due to abrasion of the catalyst particles themselves in the reactor, whereby the catalyst will be lost as accompanying the reaction gas, and not only that, the finely pulverized catalyst or a heavy metal of e.g. copper chloride as a catalyst component is likely to be included in the condensed liquid and discharged out of the system. Further, since the reactor is a single container, a special measure is required, when oxygen is supplied, to avoid burning or explosion of ethylene with such oxygen, and a problem from the viewpoint of the safety is feared such that there is a substantial possibility of danger when the reaction becomes non-uniform or when the fluidized state becomes abnormal.

In the method disclosed in U.S. Pat. No. 3,892,816 as an oxygen method employing fixed bed reactors, pure oxygen is introduced directly to a flammable ethylene or EDC in a highly concentrated state immediately before the reactors, whereby there is a possibility of burning or explosion at such an introduction point. Also in the fixed bed oxygen method disclosed in Japanese Unexamined Patent Publication No. 134295/1994, highly pure oxygen is likewise directly introduced to form a composition for combustion of ethylene and EDC, and there will be a possibility of explosion or burning, although the ethylene concentration in the recycling gas is lower than U.S. Pat. No. 3,892,816.

Further, in each of the methods disclosed in Japanese Examined Patent Publication No. 1299/1988, U.S. Pat. No. 3,892,816 and Japanese Unexamined Patent Publication No. 134295/1994, the non-condensed component after condensing and separating the gas discharged from the reactor, is used by itself as a recycling gas, whereby it is necessary to take corrosion of the apparatus into consideration, since the non-condensed gas contains a very small amount of unreacted hydrogen chloride and EDC as well as moisture.

When the superiority of a process is evaluated for industrial application of the oxy reaction, the conversions of ethylene and hydrogen chloride to EDC, i.e. the ethylene yield and the hydrogen chloride yield, have very important significance, and they must be as high as possible. Namely, a decrease in the ethylene yield means an increase in the amount of burned ethylene, the amount of by-products formed or the non-reacted amount, whereby the waste gas treating installation will be required to be of a large size, and the cost for treating the waste gas will increase. Further, the same is true with respect to the hydrogen chloride yield. Namely, a decrease in the hydrogen chloride yield means an increase in the non-reacted amount, whereby the acid concentration in water formed by the oxy reaction will be high, thus leading to an increase in the cost for treatment such as neutralization at the time of discharging the water out of the system.

Further, with respect to by-products other than EDC among chlorinated hydrocarbons which are formed by the oxy reaction, their increase naturally lowers the ethylene yield and the hydrogen chloride yield and further brings about an adverse effect such as an increase of the energy consumption in the purification treatment of EDC. Accordingly, it is necessary to increase the proportion of EDC (hereinafter referred to as the EDC purity) among the formed chlorinated hydrocarbon components as far as possible.

Therefore, it has been desired to develop a method for producing EDC in good yield under such conditions that the amount of waste gas discharged out of the system is suppressed, corrosion of the apparatus is prevented and no danger of explosion or the like is present, in carrying out the oxy reaction of ethylene, hydrogen chloride and oxygen.

The present inventors have conducted extensive studies on a method for producing EDC safely without any environmental problem and in good yield, and as a result, have found it possible to produce EDC in good yield while preventing corrosion of the apparatus and under a condition free from a danger of e.g. explosion, by specifically adjusting the composition of the non-condensed gas discharged from the oxy reactor and recycling such a gas to the oxy reactor. The present invention has been accomplished on the basis of this discovery.

SUMMARY OF THE INVENTION

That is, the present invention provides, in a method for producing 1,2-dichloroethane by an oxychlorination reaction of ethylene, hydrogen chloride and oxygen, a continuous method for producing 1,2-dichloroethane, which comprises cooling a gas discharged from an oxychlorination reactor to condense and separate 1,2-dichloroethane and water therefrom, further removing hydrogen chloride and carbon dioxide therefrom, then mixing oxygen and nitrogen thereto so that the oxygen concentration becomes from 20 to 30 vol % and the ethylene concentration becomes from 1 to 3 vol % and supplying the gas mixture thus adjusted to an oxychlorination reactor.

DESCRIPTION OF THE PREFERRED EMBODIMENTS

Now, typical embodiments of the present invention will be described in detail with reference to FIGS. 1 and 2. However, it should be understood that the present invention is by no means restricted to such FIGS. 1 and 2.

Figure 1:
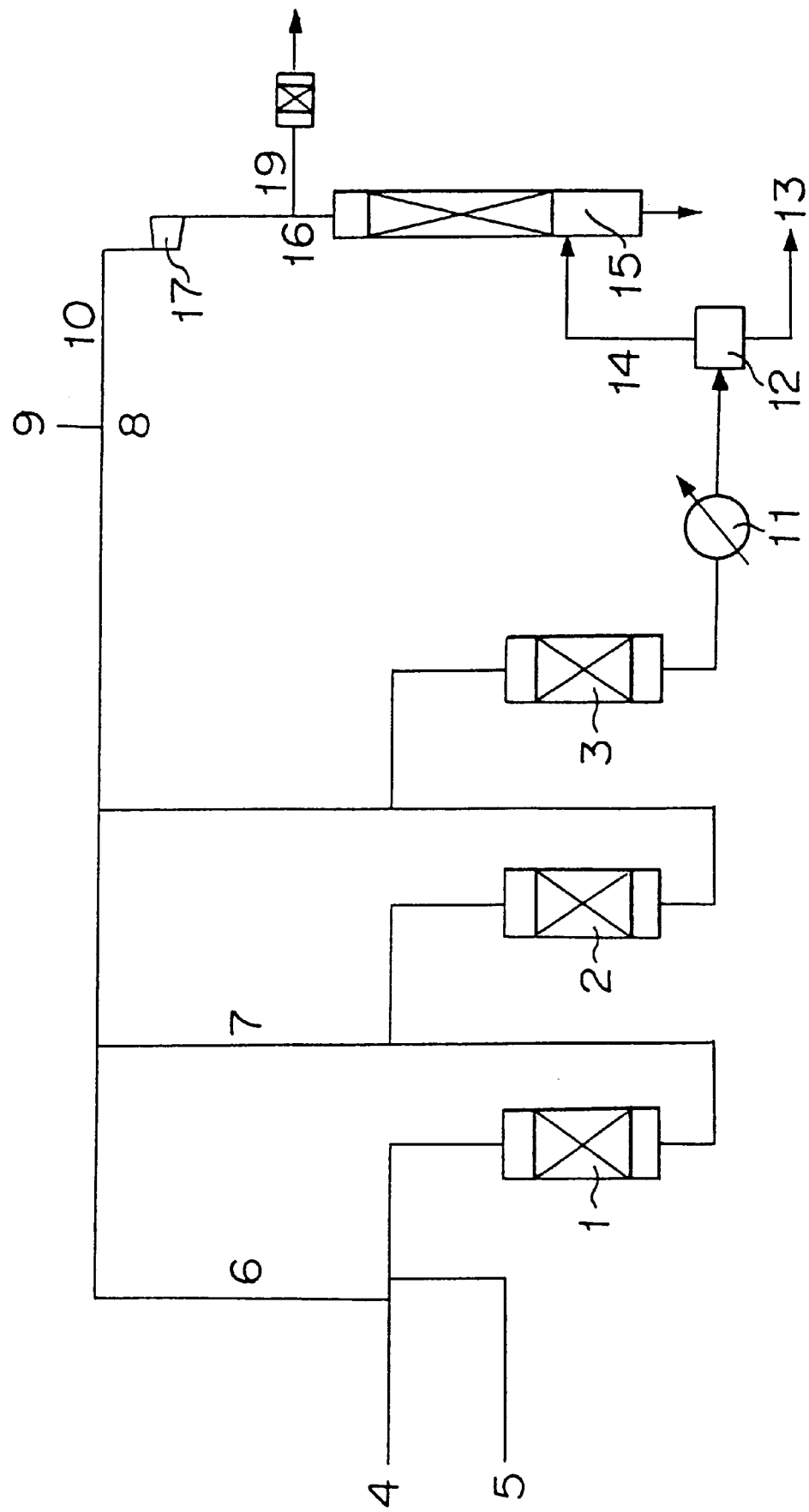
FIG. 1 is a flow sheet from a fixed bed flow reaction apparatus to a packed column used in the present invention.
Figure 2:
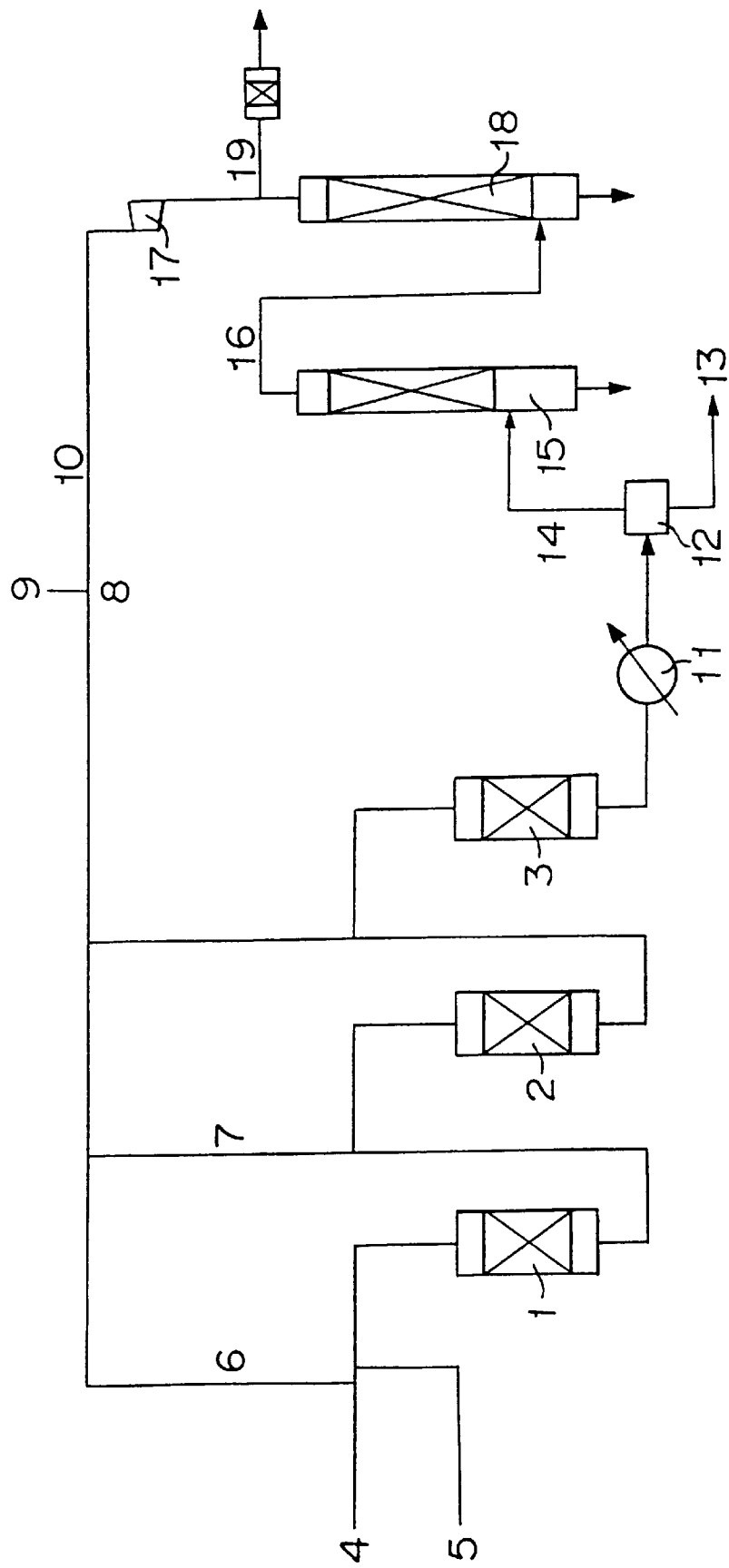
FIG. 2 is a flow sheet from a fixed bed flow reaction apparatus to a solvent-absorbing apparatus used in the present invention.

Symbols used in FIGS. 1 and 2 represent the following.

Reference numerals 1, 2 and 3 represent oxy reactors, numerals 4 and 5 conduits for introducing ethylene, hydrogen chloride, etc., respectively, numerals 6 and 7 conduits for introducing an oxygen-containing gas, numeral 8 an oxygen-mixing portion, numeral 9 a conduit for introducing oxygen and nitrogen, numeral 10 a conduit for a recycling gas, numeral 11 a heat exchanger for cooling, numeral 12 a gas-liquid separator, numeral 13 a conduit to a post treatment installation, numeral 14 a conduit, numeral 15 a packed column, numeral 16 a conduit, numeral 17 a compressor, numeral 18 an apparatus for absorbing chlorinated hydrocarbon compounds, and numeral 19 a conduit.

FIG. 1 is a basic flow sheet of the continuous method for producing EDC of the present invention, and FIG. 2 is a flow sheet of the continuous method for producing EDC having a step of absorbing chlorinated hydrocarbon compounds further added to reduce the corrosive nature of the recycling gas.

The oxy reactors 1, 2 and 3 are multitubular heat exchanger type reactors having a catalyst for the oxy reaction packed in the tubes and having a heat medium circulated around the tubes to remove the heat of reaction out of the system. For this purpose, any reactors may be employed so long as the oxy reaction can thereby be carried out. For example, fixed bed reactors or fluidized bed reactors may be mentioned.

In the present invention, it is particularly preferred to employ fixed bed reactors, since it is thereby possible to safely and efficiently carry out the reaction, and the possibility of inclusion of impurities or heavy metal components, such as finely pulverized catalyst, in the effluent from the reactors, is very low.

Further, the oxy reactors to be used in the present invention are preferably arranged so that at least three reactors are connected in series, whereby EDC can be produced safely and efficiently.

The catalyst for the reaction to be used in the present invention may be the one commonly used as a catalyst for the oxy reaction. For example, so-called Deacon catalyst particles comprising copper chloride as the main component, may be used.

The conduits 4 and 5 are designed to supply to the oxy reactors, ethylene and hydrogen chloride among the starting materials to be supplied to the oxy reactors. The conduits 6 and 7 are designed to supply an oxygen-containing gas to the respective oxy reactors. When three or more oxy reactors are arranged in series, it is preferred that ethylene and hydrogen chloride are all supplied to the oxy reactor located at the most upstream side and the oxygen-containing gas is supplied dividedly to the second and subsequent oxy reactors as counted from the upstream side, whereby EDC can be produced safely and efficiently, while avoiding a danger of explosion or burning of ethylene and EDC. Further, for the balance of reaction, it is also possible to supply the oxygen-containing gas dividedly to the third and subsequent reactors as counted from the upstream side.

In the present invention, the amount of ethylene to be supplied is not particularly limited. However, by using it slightly excessively over the stoichiometric amount relative to hydrogen chloride, it is possible to substantially reduce the unreacted amount of hydrogen chloride, and at the same time, it is possible to suppress formation of by-products such as unnecessary 1,1,2-trichloroethane and 1,1,2,2-tetrachloroethane due to too much chlorination of ethylene. However, when the amount of ethylene supplied is excessive over the stoichiometric amount relative to hydrogen chloride, non-reacted ethylene by the oxy reaction tends to increase, and the ethylene concentration at the outlet of the final reactor tends to be high. However, as will be described hereinafter, the majority will be recycled to the reactor, and the entire amount will not be lost. However, if the gas discharged from the final reactor contains ethylene in a high concentration, a large amount of ethylene is likely to accompany a part of the gas discharged out of the system, whereby the yield will, of course, decrease, and as a more serious problem, there will be a possibility of explosion at the oxgen-mixing portion 8. Whereas, in the method of the present invention, nitrogen is introduced from a conduit 9 to prevent the high concentration of ethylene. Here, if the amount of ethylene supplied relative hydrogen chloride is unnecessarily excessive, the amount of nitrogen required will also increase, which will finally lead to an increase of the amount of waste gas of the overall installation of the oxy reactors, such being undesirable. Accordingly, in the present invention, the amounts of ethylene and nitrogen to be supplied are adjusted so that the ethylene concentration will be from 1 to 3 vol %, preferably from 1.5 to 2.5 vol %, at the oxygen mixing portion, whereby it has been made possible to accomplish the condition for supplying ethylene stoichiometrically excessively relative to hydrogen chloride in the oxy reaction and the objective of avoiding a danger of explosion at the oxygen mixing portion 8.

The amount of oxygen to be supplied from the conduit 9 is preferably slightly excessive over the stoichiometric amount relative to hydrogen chloride, like the supply of ethylene. The reason for this is that oxygen will be consumed by slight burning of ethylene in the reactors, and even if a very small amount of unreacted oxygen remains, it will be supplied again to the oxy reactors as an oxygen source, whereby the starting material loss will be limited to the minimum level only with the oxygen accompanying the waste gas.

In the present invention, the oxygen source to be supplied to the oxy reactors, is an oxygen-containing gas adjusted to have an oxygen concentration of from 20 to 30 vol %, preferably from 22 to 26 vol %, by mixing a recycling gas from a conduit 10 discharged from the final reactor and subjected to a series of treatments which will be described hereinafter, with the oxygen and nitrogen from the conduit 9, at the oxygen-mixing portion 8. If the oxygen concentration of this oxygen-containing gas is low, i.e. if the amount of the recycling gas from the conduit 10 is large, the respective concentrations of ethylene, hydrogen chloride and oxygen in the oxy reactors tend to decrease, whereby the oxy reaction will be suppressed, and the residence time in the reactors i.e. the reaction time tends to be short, whereby the amount of EDC produced, tends to decrease, whereby the reaction will be inefficient, such being undesirable. On the other hand, if the oxygen concentration in the oxygen-containing gas is high, i.e. if the amount of the recycling gas from the conduit 10 is suppressed, the passing speed through the oxy reactors tends to be slow, whereby a local run away reaction is likely to occur in the catalyst layer, or formation of unnecessarily highly chlorinated by-products such as 1,1,2-trichloroethane and 1,1,2,2-tetrachloroethane, tend to increase, whereby the purity of formed EDC decreases, such being undesirable. Accordingly, in the present invention, the oxygen concentration in the oxygen-containing gas is from 20 to 30 vol %, whereby the highly pure EDC can be produced efficiently, and the production can be carried out under a stabilized condition.

In the present invention, the oxygen and nitrogen to be used for adjusting the composition of the oxygen-containing gas may be in any state so long as the oxygen-containing gas composition in the present invention can thereby be attained. For example, air, a gas mixture having the compositional proportions of oxygen and nitrogen adjusted, pure oxygen and pure nitrogen may be mentioned. It is preferred to employ highly pure oxygen and highly pure nitrogen separated from e.g. air, or a gas mixture of oxygen and nitrogen adjusted to efficiently bring the oxygen concentration to from 20 to 30 vol % and the ethylene concentration to from 1 to 3 vol %, so that the reaction can efficiently be carried out, and the gas formation can be minimized.

The fluid after the reaction has been carried out in the oxy reactors under such conditions for supplying ethylene, hydrogen chloride and the oxygen-containing gas, will be cooled by a directly connected heat exchanger 11 to a temperature of about 40° C. in the vicinity of room temperature, whereupon the majorities of water and EDC formed by the oxy reaction will be condensed and liquefied and separated by a gas-liquid separator 12, and they will be led by a conduit 13 to a post treating installation, where they will be treated as a product.

In this post treating step, if the purity of EDC is low, the load on the purification installation will naturally be large, such being inefficient. Further, with respect to the formed water, if its acid concentration is high, not only the loss of hydrogen chloride will be substantial, but also it will be necessary to carry out neutralization or the like at the time of discharging the formed water out of the system. Accordingly, it is desired that the EDC purity is brought to be as high as possible, and the acid concentration in the formed water is brought to be as low as possible. A production method satisfying such conditions can be regarded as a better method for producing 1,2-dichloroethane.

As indexes for conversions of ethylene and hydrogen chloride to EDC, the ethylene yield and the hydrogen chloride yield are employed. These yields decrease if the purity of EDC is low, if the acid concentration in the formed water increases, if the loss of hydrogen chloride increases, or if unreacted ethylene increases in the waste gas. A production method in which such yields are high can be regarded as a better method for producing 1,2-dichloroethane.

The gas component after the gas-liquid separation is supplied through a conduit 14 to a packed column 15 and treated to remove residual unreacted hydrogen chloride and a very small amount of carbon dioxide formed by combustion of ethylene, contained in the gas component. By removing hydrogen chloride from the gas component, the corrosiveness of the gas component will be low or eliminated. On the other hand, with respect to carbon dioxide, although it does not directly affect the reaction, if carbon dioxide accumulates unnecessarily in the system, not only the composition of the gas component to be recycled, will be unstable, but also it promotes high concentration of carbon monooxide which is a flammable gas formed by combustion of ethylene, whereby there will be a possible danger of an explosion reaction thereof with oxygen.

Accordingly, in the present invention, from the gas component after the gas-liquid separation, hydrogen chloride is removed, whereby the corrosiveness of the gas component can be reduced, and carbon dioxide is removed, whereby conversion of carbon monooxide to carbon dioxide will be promoted, and it is possible to prevent high concentration of carbon monooxide as a flammable gas, whereby production of EDC can be conducted safely.

In the present invention, there is no particular restriction as to the apparatus to be used for removing hydrogen chloride and carbon dioxide, and any apparatus can be used so long as it is capable of removing hydrogen chloride and carbon dioxide. For example, a packed column may be mentioned. As such a packed column, it is preferred to employ a column in which the gas to be treated can be countercurrently contacted with a solution of a base such as sodium hydroxide or potassium hydroxide, whereby hydrogen chloride and carbon dioxide can efficiently be removed.

In the present invention, the gas having hydrogen chloride and carbon dioxide removed, may be supplied through a conduit 16, pressurized by a compressor 17 and sent through a conduit 10 to an oxygen mixing portion 8 without any substantial problem. However, as shown in FIG. 2, treatment by an apparatus 18 for absorbing chlorinated hydrocarbons such as EDC, may further be carried out. By using such an absorbing apparatus 18, it is possible to completely prevent corrosion by an acid component which is generated by decomposition of EDC, etc. due to a temperature increase in the compressor 17, whereby it is also possible to prevent useless return of EDC to the oxy reaction.

In the present invention, the absorbing apparatus which is used as the case requires, is not particularly limited, and may be of a packed column type which is commonly used for countercurrent contact with an organic solvent.

In the present invention, highly corrosive hydrogen chloride is removed by an apparatus represented by the packed column 15, and in some cases, chlorinated hydrocarbons are removed by an apparatus represented by the absorbing apparatus 18, whereby the conduits 15 and 10, the compressor 17 and the oxygen mixing portion 8 and in some cases, the absorbing apparatus 18 located after the packed column 15, can be made of commonly used inexpensive carbon steel material, which is economically advantageous.

In the present invention, the excess gas other than the one used to maintain the oxygen concentration at a level of from 20 to 30 vol %, preferably from 22 to 26 vol %, will be discharged as a waste gas out of the system by a conduit 19 prior to the compressor 17, while maintaining the pressure in the system to be constant.

The waste gas discharged through this conduit 19 is free from corrosiveness or a danger of combustion or explosion, as mentioned above, and thus may be discharged as it is, out of the system. However, in some cases, it may contain a very small amount of EDC, and it is preferred to subject it to EDC recovery treatment.

Further, in order to avoid an adverse effect of a condensed component of water or EDC contained in a very small amount in the recycling gas to be brought into the compressor 17, it is preferred to preheat the gas at a position of the conduit 16 immediately prior to the introduction. Likewise, in order to prevent dew-point corrosion due to hydrogen chloride at the position for introducing the oxygen containing gas comprising oxygen and nitrogen to the oxy reactors, it is preferred to take a proper measure such as preheating the conduits 6, 7, 8 and 10.

As described in the foregoing, by conducting the oxy reaction of ethylene with hydrogen chloride and oxygen in accordance with the method of the present invention, it is possible to suppress the amount of the waste gas discharged out of the system to a minimum level to prevent corrosion of the apparatus and to obtain EDC in good yield under a condition free from a danger of explosion, etc.

Now, the present invention will be described in detail with reference to Examples. However, it should be understood that the present invention is by no means restricted to such specific Examples.

In Examples and Comparative Examples, the oxy reaction of ethylene, hydrogen chloride and oxygen was carried out by using an apparatus having three reactors connected in series, as shown in FIG. 1, or an apparatus provided further with a chlorinated hydrocarbon compounds absorbing apparatus as shown in FIG. 2.

Figure 4:
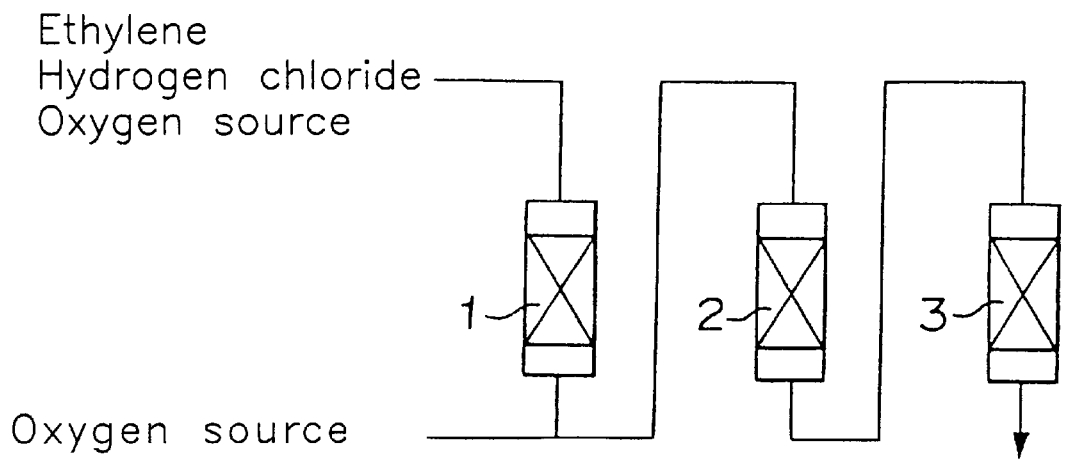
FIG. 4 is a flow sheet for a series of fixed bed flow reaction apparatus.

FIG. 4 illustrates the details of the oxy reactors 1, 2 and 3. They are of the same type, and each of them is a fixed bed catalyst reactor of a multitubular heat exchanger type having a structure comprising three stainless tubes of 34 mm in diameter×4,000 mm having a Deacon catalyst packed inside and having a heat medium circulated outside the tubes to remove the heat generated by the reaction.

EXAMPLE 1

Using the apparatus as shown in FIG. 1, feed materials in the amounts as shown in Table 1 were supplied to the oxy reactors 1, 2 and 3 by the respective conduits. At that time, the gas component after removing the majority of EDC, water, etc. from the fluid after the oxy reaction by a series of treatments as described hereinafter, was pressurized by the compressor 17 and then mixed with oxygen and nitrogen introduced from the conduit 9 at the oxygen mixing portion 8 to form an oxygen-containing gas. This oxygen-containing gas was introduced to the oxy reactors 1 and 2 in a ratio of 7:3 from the conduits 6 and 7, respectively. The inlet temperature of each oxy reactor was set to be at least 200° C., and the inlet pressure at the oxy reactor 1 was set to be 385 kPa. Thus, production of EDC was carried out. To obtain EDC, the gas discharged from the final oxy reactor was cooled by the heat exchanger 11 for cooling to a temperature of 40° C. and then subjected to the gas-liquid separator 12, whereby the majority of the formed water and EDC were separated and recovered.

Then, in the next packed column 15 (alkali-washing apparatus), the acid component in the non-condensed gas was neutralized and carbon dioxide was removed. At the same time, the gas was cooled to 20° C., whereby a small amount of EDC was again condensed and recovered.

Such feeding conditions, the waste gas discharged out of the system and the analytical results after the reaction are shown in Table 1.

The ethylene yield and the hydrogen chloride yield presented in Table 1 were calculated by the following formulas.

Ethylene yield(%)=the amount of ethylene converted to EDC/the amount of ethylene supplied×100

Hydrogen chloride yield(%)=the amount of the hydrogen chloride converted to EDC/the amount of hydrogen chloride supplied×100

As a result, the amount of the waste gas generated was very small, and the composition of each of the waste gas and the oxygen-containing gas was outside the range for explosion of a flammable gas mixture and non-corrosive gas, and it was the one having carbon dioxide completely removed, whereby it was possible to carry out the operation safely and in a stabilized condition. Further, the obtained EDC was highly pure, and the ethylene yield and the hydrogen chloride yield were high. Thus, the method was highly efficient.

The operation was carried out under these conditions continuously for 6 months, whereby no deterioration of the catalyst was observed, and no corrosion or property change was observed in the apparatus, piping, etc., and the operation was carried out safely and in a stabilized condition.

COMPARATIVE EXAMPLE 1

Using the apparatus as shown in FIG. 1, feed materials in the amounts as shown in Table 1 were supplied to the oxy reactors by the respective conduits. Particularly, the ethylene concentration in the oxygen-containing gas was adjusted to be 0.57 vol %. Then, the production of EDC was carried out in the same manner as in Example 1.

The waste gas discharged out of the system and the analytical results after the reaction are shown in Table 1.

In the system (the oxygen-containing gas and the waste gas), the amount of carbon monooxide as a flammable gas increased, the ethylene yield and the hydrogen chloride yield were low, and the purity of EDC was low.

COMPARATIVE EXAMPLE 2

Using the apparatus as shown in FIG. 1, feed materials in the amounts as identified in Table 1 were supplied to the oxy reactors by the respective conduits. Particularly, the ethylene concentration in the oxygen-containing gas was adjusted to be 3.05 vol %. Then, the production of EDC was carried out in the same manner as in Example 1.

The waste gas discharged out of the system and the analytical results after the reaction are shown in Table 1.

In the system (the oxygen-containing gas and the waste gas), the amount of carbon monooxide as a flammable gas increased, the ethylene yield and the hydrogen chloride yield were low, and the purity of EDC was low.

EXAMPLE 2

Using the apparatus as shown in FIG. 1, feed materials in the amounts as identified in Table 2 were supplied to the oxy reactors by the respective conduits. Particularly, the oxygen concentration in the oxygen-containing gas was adjusted to be 22 vol %. Then, the production of EDC was carried out in the same manner as in Example 1.

The waste gas discharged out of the system and the analytical results after the reaction are shown in Table 2.

As a result, the amount of the waste gas generated was very small, the composition of the oxygen-containing gas was outside the range for explosion of a flammable gas mixture and non-corrosive gas, and it was the one having carbon dioxide completely removed, whereby it was possible to carry out the operation safely and in a stabilized condition. Further, the obtained EDC was highly pure, the ethylene yield and the hydrogen chloride yield were high, and the method was highly efficient.

COMPARATIVE EXAMPLE 3

Using the apparatus shown in FIG. 1, feed materials in the amounts as identified in Table 2 were supplied to the oxy reactors by the respective conduits. Particularly, the oxygen concentration in the oxygen-containing gas was adjusted to be 18.20 vol %. Then, the production of EDC was carried out in the same manner as in Example 1.

The waste gas discharged out of the system and the analytical results after the reaction are shown in Table 2.

The ethylene yield and the hydrogen chloride yield were low, and the purity of EDC was low.

COMPARATIVE EXAMPLE 4

Using the apparatus as shown in FIG. 1, feed materials in the amounts identified in Table 2 were supplied to the oxy reactors by the respective conduits. Particularly, the oxygen concentration in the oxygen-containing gas was adjusted to be 31.50 vol %. Then, the production of EDC was carried out in the same manner as in Example 1.

The waste gas discharged out of the system and the analytical results after the reaction are shown in Table 2.

In the system (the oxygen-containing gas and the waste gas), the amount of carbon monooxide as a flammable gas increased, the ethylene yield and the hydrogen chloride yield were low, and the purity of EDC was low.

EXAMPLE 3

Using the apparatus as shown in FIG. 2 having a chlorinated hydrocarbon compounds-absorbing apparatus 18 (a solvent absorbing apparatus), feed materials in the amounts as identified in Table 3 were supplied by the respective conduits.

The waste gas discharged out of the system and the analytical results after the reaction are shown in Table 3.

As a result, the amount of the waste gas generated was very small, the composition of each of the waste gas and the oxygen-containing gas was outside the range for explosion of a flammable gas mixture and non-corrosive gas, and it was the one having carbon dioxide completely removed, whereby it was possible to carry out the operation safely and in a stabilized condition. Further, the obtained EDC was highly pure, the ethylene yield and the hydrogen chloride yield were high, and the method was highly efficient.

COMPARATIVE EXAMPLE 5

Using an apparatus having the packed column 15 (the alkali washing apparatus) removed from the apparatus shown in FIG. 1, i.e. an apparatus incapable of removing hydrogen chloride and carbon dioxide since no alkali washing of the non-condensed gas discharged after the reaction, was conducted, feed materials in the amounts as identified in Table 3 were supplied by the respective conduits, and the production of EDC was carried out.

The waste gas discharged out of the system and the analytical results after the reaction are shown in Table 3.

In the non-condensed gas, strongly corrosive unreacted hydrogen chloride was observed. Further, the compositions of the oxygen-containing gas and the waste gas were very unstable, and an abrupt increase of carbon monooxide in the oxygen-containing gas was observed, and the composition became a dangerous state. Therefore, the production was stopped. Further, the ethylene yield and the hydrogen chloride yield were low, and the purity of EDC was low.

EXAMPLE 4

Using the apparatus as shown in FIG. 2 having a chlorinated hydrocarbon compounds-absorbing apparatus 18 (a solvent absorbing apparatus), feed materials in the amounts as identified in Table 4 were supplied by the respective conduits.

The waste gas discharged out of the system and the analytical results after the reaction are shown in Table 4.

As a result, the amount of the waste gas discharged was very small, and the composition of the oxygen-containing gas was outside the range for explosion of a flammable gas mixture and contains no substantial remaining chlorinated hydrocarbons. Therefore, it was non-corrosive gas, and the one having carbon dioxide completely removed, whereby it is possible to carry out the operation safely in a stabilized condition. Further, the obtained EDC was highly pure, the ethylene yield and the hydrogen chloride yield were high, and the method was highly efficient.

COMPARATIVE EXAMPLE 6

Figure 3:
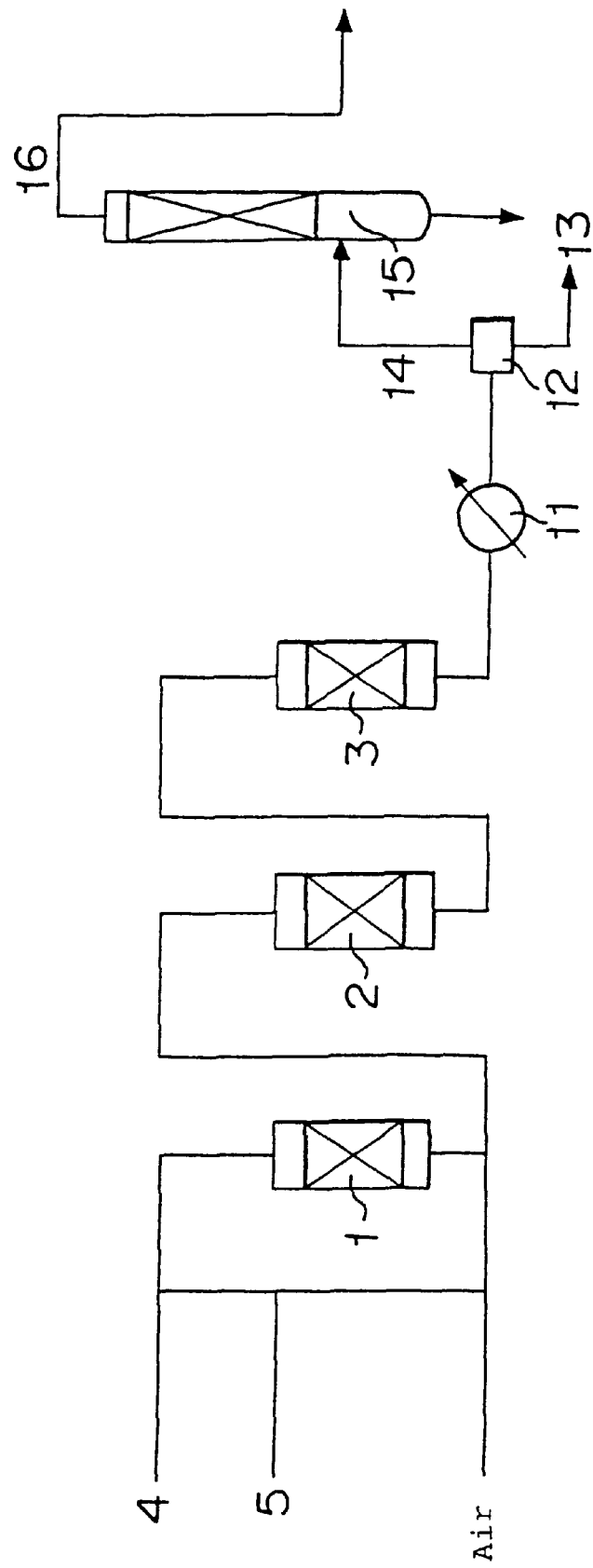
FIG. 3 is a flow sheet of a fixed bed flow reaction apparatus for an air method.

Using the apparatus as shown in FIG. 3 using air as the oxygen source, an ethylene and air as the oxygen source were introduced so that the stoichiometric ratios to hydrogen chloride would be the same as in Example 4, and the production of EDC was carried out.

The waste gas discharged out of the system and the analytical results after the reaction are shown in Table 4.

The amount of the waste gas was very large, the ethylene yield and the hydrogen chloride yield were low, and the purity of EDC was low.

TABLE 1

|  | Example 1 | Comparative Example 1 | Comparative Example 2 |
|---|---|---|---|
| Alkali washing apparatus | Present | Present | Present |
| Solvent absorbing apparatus | Absent | Absent | Absent |
| Feed materials |  |  |  |
| Ethylene supplied (Nm$^3$/hr) | 2.33 | 2.41 | 2.30 |
| Hydrogen chloride supplied (Nm$^3$/hr) | 4.65 | 4.65 | 4.65 |
| Oxygen supplied (Nm$^3$/hr) | 1.22 | 1.23 | 1.10 |
| Nitrogen supplied (Nm$^3$/hr) | 0.092 | 0.093 | 0.083 |
| Oxygen-containing gas |  |  |  |
| Amount supplied (Nm$^3$/hr) | 5.65 | 5.48 | 5.52 |
| Composition of oxygen-containing gas |  |  |  |
| Ethylene (vol %) | 1.97 | 0.57 | 3.05 |
| Oxygen (vol %) | 23.65 | 24.45 | 24.20 |
| Carbon monoxide (vol %) | 3.54 | 5.54 | 8.22 |
| Carbon dioxide (vol %) | 0.0 | 0.0 | 0.0 |
| EDC (vol %) | 1.33 | 1.05 | 1.92 |
| Nitrogen etc. (vol %) | 69.51 | 68.39 | 62.61 |
| Waste gas |  |  |  |
| Amount discharged (Nm$^3$/hr) | 0.105 | 0.106 | 0.102 |
| Composition of waste gas |  |  |  |
| Ethylene (vol %) | 2.57 | 0.75 | 4.10 |
| Oxygen (vol %) | 2.67 | 2.66 | 0.60 |
| Carbon monoxide (vol %) | 4.61 | 7.30 | 11.04 |
| Carbon dioxide (vol %) | 0.0 | 0.0 | 0.0 |
| EDC (vol %) | 1.73 | 1.38 | 2.58 |
| Other chlorinated hydrocarbons (vol %) | 0.80 | 0.79 | 0.74 |
| Nitrogen etc. (vol %) | 87.63 | 87.12 | 80.94 |
| Reaction products |  |  |  |
| EDC purity (%) | 98.7 | 97.5 | 97.8 |
| Formed water (g/l) | 12.0 | 110.9 | 50.8 |
| Ethylene conversion (%) | 97.6 | 96.5 | 96.6 |
| Hydrogen chloride conversion (%) | 98.4 | 96.8 | 97.1 |

TABLE 2

|  | Example 2 | Comparative Example 3 | Comparative Example 4 |
|---|---|---|---|
| Alkali washing apparatus | Present | Present | Present |
| Solvent absorbing apparatus | Absent | Absent | Absent |
| Feed materials |  |  |  |
| Ethylene supplied (Nm$^3$/hr) | 2.33 | 2.32 | 2.33 |
| Hydrogen chloride supplied (Nm$^3$/hr) | 4.65 | 4.65 | 4.65 |
| Oxygen supplied (Nm$^3$/hr) | 1.22 | 1.18 | 1.22 |
| Nitrogen supplied (Nm$^3$/hr) | 0.092 | 0.089 | 0.092 |
| Oxygen-containing gas |  |  |  |
| Amount supplied (Nm$^3$/hr) | 6.08 | 7.35 | 4.25 |
| Composition of oxygen-containing gas |  |  |  |
| Ethylene (vol %) | 1.83 | 1.65 | 2.62 |
| Oxygen (vol %) | 22.00 | 18.20 | 31.50 |
| Carbon monoxide (vol %) | 3.22 | 3.56 | 6.05 |
| Carbon dioxide (vol %) | 0.0 | 0.0 | 0.0 |
| EDC (vol %) | 1.52 | 1.03 | 1.86 |
| Nitrogen etc. (vol %) | 72.43 | 75.56 | 57.97 |
| Waste gas |  |  |  |
| Amount discharged (Nm$^3$/hr) | 0.104 | 0.100 | 0.115 |
| Composition of waste gas |  |  |  |
| Ethylene (vol %) | 2.33 | 1.99 | 3.79 |
| Oxygen (vol %) | 2.46 | 2.59 | 4.01 |
| Carbon monoxide (vol %) | 4.11 | 4.30 | 8.76 |
| Carbon dioxide (vol %) | 0.0 | 0.0 | 0.0 |
| EDC (vol %) | 1.94 | 1.25 | 2.69 |
| Other chlorinated hydrocarbons (vol %) | 0.80 | 0.80 | 0.79 |
| Nitrogen etc. (vol %) | 88.36 | 89.07 | 80.02 |
| Reaction products |  |  |  |
| EDC purity (%) | 98.6 | 97.5 | 96.9 |
| Formed water (g/l) | 38.5 | 140.1 | 45.0 |
| Ethylene conversion (%) | 97.5 | 96.4 | 95.7 |
| Hydrogen chloride conversion (%) | 98.4 | 97.3 | 96.9 |

TABLE 3

|  | Example 3 | Comparative Example 5 |
|---|---|---|
| Alkali washing apparatus | Present | Absent |
| Solvent absorbing apparatus | Present | Absent |
| Feed materials |  |  |
| Ethylene supplied (Nm$^3$/hr) | 2.34 | 2.33 |
| Hydrogen chloride supplied (Nm$^3$/hr) | 4.65 | 4.65 |
| Oxygen supplied (Nm$^3$/hr) | 1.23 | 1.22 |
| Nitrogen supplied (Nm$^3$/hr) | 0.093 | 0.092 |
| Oxygen-containing gas |  |  |
| Amount supplied (Nm$^3$/hr) | 5.43 | 5.56 |
| Composition of oxygen-containing gas |  |  |
| Ethylene (vol %) | 1.86 | 2.01 |
| Oxygen (vol %) | 24.60 | 24.11 |
| Carbon monoxide (vol %) | 3.56 | 11.22 |
| Carbon dioxide (vol %) | 0.0 | 8.21 |
| EDC (vol %) | 0.01 | 3.32 |
| Nitrogen etc. (vol %) | 70.01 | 51.13 |
| Waste gas |  |  |
| Amount discharged (Nm$^3$/hr) | 0.104 | 0.143 |
| Composition of waste gas |  |  |
| Ethylene (vol %) | 2.46 | 2.62 |
| Oxygen (vol %) | 2.65 | 2.85 |
| Carbon monoxide (vol %) | 4.65 | 14.68 |
| Carbon dioxide (vol %) | 0.0 | 10.74 |
| EDC (vol %) | 0.01 | 4.35 |
| Other chlorinated hydrocarbons (vol %) | 0.01 | 0.59 |
| Nitrogen etc. (vol %) | 90.22 | 64.17 |
| Reaction products |  |  |
| EDC purity (%) | 98.6 | 97.9 |
| Formed water (g/l) | 14.5 | 70.4 |
| Ethylene conversion (%) | 97.5 | 96.7 |
| Hydrogen chloride conversion (%) | 98.5 | 97.6 |

TABLE 4

|  | Example 4 | Comparative Example 6 |
|---|---|---|
| Alkali washing apparatus | Present | Absent |
| Solvent absorbing apparatus | Present | Absent |
| Feed materials |  |  |
| Ethylene supplied (Nm$^3$/hr) | 3.03 | 2.44 |
| Hydrogen chloride supplied (Nm$^3$/hr) | 6.05 | 4.65 |
| Oxygen supplied (Nm$^3$/hr) | 1.59 | — |
| Nitrogen supplied (Nm$^3$/hr) | 0.120 | — |
| Oxygen-containing gas |  |  |
| Amount supplied (Nm$^3$/hr) | 7.20 | 6.38 (air) |
| Composition of oxygen-containing gas |  |  |
| Ethylene (vol %) | 2.03 | — |
| Oxygen (vol %) | 24.20 | 20.94 |
| Carbon monoxide (vol %) | 5.12 | — |
| Carbon dioxide (vol %) | 0.0 | 0.04 |
| EDC (vol %) | 0.01 | — |
| Nitrogen etc. (vol %) | 68.64 | 79.02 |
| Waste gas |  |  |
| Amount discharged (Nm$^3$/hr) | 0.138 | 5.47 |
| Composition of waste gas |  |  |
| Ethylene (vol %) | 2.66 | 1.10 |
| Oxygen (vol %) | 2.79 | 1.80 |
| Carbon monoxide (vol %) | 6.71 | 1.43 |
| Carbon dioxide (vol %) | 0.0 | 0.90 |
| EDC (vol %) | 0.01 | 1.50 |
| Other chlorinated hydrocarbons (vol %) | 0.01 | 0.98 |
| Nitrogen etc. (vol %) | 87.82 | 92.29 |
| Reaction products |  |  |
| EDC purity (%) | 98.2 | 98.6 |
| Formed water (g/l) | 48.2 | 85.0 |
| Ethylene conversion (%) | 97.1 | 96.2 |
| Hydrogen chloride conversion (%) | 98.5 | 96.7 |

By conducting the oxy chlorination reaction in accordance with the method of the present invention, the process will be safe, and the amount of the waste gas can substantially be reduced, whereby it has been made possible to produce 1,2-dichloroethane efficiently.

What is claimed is:

1. In a method for producing 1,2-dichloroethane by an oxychlorination reaction of ethylene, hydrogen chloride and oxygen, a continuous method for producing 1,2-dichloroethane, which comprises cooling a gas discharged from an oxychlorination reactor to condense and separate 1,2-dichloroethane and water therefrom, further removing hydrogen chloride and carbon dioxide therefrom, then mixing oxygen and nitrogen thereto so that the oxygen concentration becomes from 20 to 30 vol % and the ethylene concentration becomes from 1 to 3 vol % and supplying the gas mixture thus adjusted to an oxychlorination reactor.

2. The continuous method for producing 1,2-dichloroethane according to claim 1, wherein after the removal of hydrogen chloride and carbon dioxide, residual chlorinated hydrocarbon compounds are further removed, then oxygen and nitrogen are mixed so that the oxygen concentration becomes from 20 to 30 vol % and the ethylene concentration becomes from 1 to 3 vol %, and the gas mixture thus adjusted is supplied to an oxychlorination reactor.

3. The continuous method for producing 1,2-dichloroethane according to claim 1, wherein ethylene and hydrogen chloride as starting materials are supplied only to one reactor located on the most upstream side of at least three oxychlorination reactors arranged in series, and the gas adjusted so that the oxygen concentration becomes from 20 to 30 vol % and the ethylene concentration becomes from 1 to 3 vol %, is dividedly supplied to the second and subsequent reactors as counted from the upstream side of the at least three oxychlorination reactors arranged in series.

4. The continuous method for producing 1,2-dichloroethane according to claim 2, wherein ethylene and hydrogen chloride as starting materials are supplied only to one reactor located on the most upstream side of at least three oxychlorination reactors arranged in series, and the gas adjusted so that the oxygen concentration becomes from 20 to 30 vol % and the ethylene concentration becomes from 1 to 3 vol %, is dividedly supplied to the second and subsequent reactors as counted from the upstream side of the at least three oxychlorination reactors arranged in series.

5. The continuous method for producing 1,2-dichloroethane according to claim 1, wherein oxychlorination reactor is a fixed bed reactor.

6. The continuous method for producing 1,2-dichloroethane according to claim 2, wherein oxychlorination reactor is a fixed bed reactor.

7. The continuous method for producing 1,2-dichloroethane according to claim 3, wherein oxychlorination reactor is a fixed bed reactor.

8. The continuous method for producing 1,2-dichloroethane according to claim 4, wherein oxychlorination reactor is a fixed bed reactor.

* * * * *

UNITED STATES PATENT AND TRADEMARK OFFICE

CERTIFICATE OF CORRECTION

PATENT NO.     : 5,905,177
DATED          : May 18, 1999
INVENTOR(S)    : SEO et al

It is certified that error appears in the above-identified patent and that said letters patent is hereby corrected as shown below:

On the title page, item [30], Foreign Application Priority Data, should read:

Apr. 20, 1995      [JP]     Japan..................................7-94974

Signed and Sealed this

Sixteenth Day of November, 1999

Attest:

Q. TODD DICKINSON

*Attesting Officer*      *Acting Commissioner of Patents and Trademarks*